United States Patent
Rebholz et al.

(10) Patent No.: US 10,448,814 B2
(45) Date of Patent: Oct. 22, 2019

(54) INSUFFLATION AND IRRIGATION VALVE, AND ENDOSCOPE WITH AN INSUFFLATION AND IRRIGATION VALVE

(71) Applicant: Karl Storz SE & Co. KG, Tuttlingen (DE)

(72) Inventors: Clemens Rebholz, Uhldingen-Muehlhofen (DE); Peter Tobien, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 104 days.

(21) Appl. No.: 14/857,533

(22) Filed: Sep. 17, 2015

(65) Prior Publication Data

US 2016/0081538 A1    Mar. 24, 2016

(30) Foreign Application Priority Data

Sep. 18, 2014  (DE) .................. 10 2014 113 472

(51) Int. Cl.
*A61B 1/015*    (2006.01)
*A61B 1/00*    (2006.01)
*G02B 23/24*    (2006.01)

(52) U.S. Cl.
CPC .......... *A61B 1/015* (2013.01); *A61B 1/00068* (2013.01); *A61B 1/00128* (2013.01); *G02B 23/2476* (2013.01)

(58) Field of Classification Search
CPC . A61B 1/00119; A61B 1/00137; A61B 1/015; A61B 1/00128; A61B 1/00068; G02B 23/2476
See application file for complete search history.

(56) References Cited

U.S. PATENT DOCUMENTS 4,325,362 A * 4/1982 Ouchi .................. A61B 1/12
                                                    600/158
4,361,138 A * 11/1982 Kinoshita .......... A61B 1/00068
                                                    600/159

(Continued)

FOREIGN PATENT DOCUMENTS

EP       1707107 A1     10/2006
JP     S57103621 A       6/1982

(Continued)

OTHER PUBLICATIONS

German Search Report Application No. DE 102 014 113 472.9 Completed: May 8, 2015; dated May 13, 2015 9 pages.

(Continued)

*Primary Examiner* — Anh Tuan T Nguyen
*Assistant Examiner* — Genja M Frankert
(74) *Attorney, Agent, or Firm* — Whitmyer IP Group LLC

(57) ABSTRACT

An insufflation and irrigation valve for an endoscope including a valve housing with a substantially cylindrical bore closed at one end by a bottom into which a gas inlet and outlet, and an irrigation inlet and outlet open, an outer plunger which is movable in the bore between an open position, in which the irrigation outlet is connected to the inlet, and a closed position, and an inner plunger movable in a longitudinal bore of the outer plunger, open toward the bottom, for connecting the gas outlet to the gas inlet in a position near the bottom and for separating the gas outlet from the gas inlet in a position remote from the bottom, wherein the gas inlet opens into the bore of the valve housing at a location nearer the bottom than the gas outlet.

12 Claims, 3 Drawing Sheets

(56) References Cited

U.S. PATENT DOCUMENTS

| | | | | | |
|---|---|---|---|---|---|
| 4,537,209 | A | * | 8/1985 | Sasa | A61B 1/00137 134/102.1 |
| 4,694,821 | A | * | 9/1987 | Kondo | A61B 1/12 600/158 |
| 4,800,869 | A | * | 1/1989 | Nakajima | A61B 1/00068 600/158 |
| 5,027,791 | A | * | 7/1991 | Takahashi | A61B 1/00068 600/158 |
| 5,427,144 | A | * | 6/1995 | Teets | A61B 1/00068 137/614.2 |
| 5,840,016 | A | * | 11/1998 | Kitano | A61B 1/12 251/335.2 |
| 6,346,075 | B1 | * | 2/2002 | Arai | A61B 1/015 600/159 |
| 2006/0041190 | A1 | * | 2/2006 | Sato | A61B 1/00068 600/159 |
| 2008/0200764 | A1 | * | 8/2008 | Okada | A61B 1/00068 600/157 |
| 2010/0087710 | A1 | * | 4/2010 | Weldon | A61B 1/018 600/123 |
| 2010/0317922 | A1 | * | 12/2010 | Kumai | A61B 1/00068 600/118 |
| 2012/0071843 | A1 | * | 3/2012 | Yamane | A61B 1/00068 604/319 |
| 2015/0011831 | A1 | * | 1/2015 | Ouchi | A61B 1/00068 600/159 |
| 2015/0257634 | A1 | * | 9/2015 | Nakade | A61B 1/00068 600/159 |
| 2016/0022127 | A1 | * | 1/2016 | Iwasaki | A61B 1/00068 15/3.5 |

FOREIGN PATENT DOCUMENTS

| | | |
|---|---|---|
| JP | H0751222 A | 2/1995 |
| JP | 2009039463 A | 2/2009 |
| JP | 2010268866 A | 12/2010 |
| JP | 2012249654 A | 12/2012 |

OTHER PUBLICATIONS

European Search Report Applicaiton No. 15185061.7 Completed: Feb. 4, 2016; dated Feb. 19, 2016 7 pages.

* cited by examiner

INSUFFLATION AND IRRIGATION VALVE, AND ENDOSCOPE WITH AN INSUFFLATION AND IRRIGATION VALVE

FIELD OF THE INVENTION

The present invention relates to an insufflation and irrigation valve according to the preamble of the invention, and to an endoscope with an insufflation and irrigation valve of this kind.

BACKGROUND OF THE INVENTION

To perform an endoscopy procedure, it is often necessary to create a hollow space inside the body. For this purpose, a gas, for example air or $CO_2$, is usually conveyed from a proximal end area of an endoscope (area near the user) through a line extending inside the shank of the endoscope to the distal end of the endoscope (end remote from the user). It emerges there at a suitable pressure and, in the area of the distal end of the endoscope, creates a hollow space within which the procedure can be performed with endoscopic monitoring. Since the distal window of the endoscopic lens system can become soiled during the procedure, as a result of which the view is impaired, an irrigation liquid can be conveyed through the shank of the endoscope to the distal end of the endoscope in order to use this liquid to clean the distal window during the endoscopy procedure. Moreover, a suction system can be provided, with which the irrigation liquid and, if appropriate, any detached pieces of tissue can be aspirated from the operating site.

To control the insufflation and irrigation in known endoscopes, a manually operable insufflation and irrigation valve is arranged on the handle of the endoscope. A proximal portion of an insufflation line is attached to a valve housing of the known insufflation and irrigation valve, via which proximal portion an insufflator can be connected to the endoscope so as to make available the insufflation gas at the required pressure. Moreover, a proximal portion of an irrigation line is attached to the valve housing, in which line an irrigation liquid from a storage container is likewise made available at a suitable pressure. A distal portion of the insufflation line and a distal portion of the irrigation line, through which the insufflation gas and the irrigation liquid can be conveyed to the distal end of the endoscope, are also attached to the valve housing. The insufflation and irrigation valve comprises a plunger which is arranged movably in the valve housing and which can be actuated by a valve button, wherein the proximal portion and the distal portion of the irrigation line can be connected to each other or separated from each other by movement of the plunger. The valve button and the plunger each have a bore which at one end is connected to the proximal portion of the insufflation line and at the other end terminates in an opening through which the insufflation gas can escape to the environment. When the opening is closed with a finger by the user, pressure is able to build up in the insufflation line and insufflation can take place. When the insufflation and irrigation valve is pressed in by further pressure from the finger, the distal portion is connected to the proximal portion of the irrigation line, such that irrigation liquid can flow to the distal end of the endoscope.

In the non-actuated state of the valve, i.e. when neither irrigation nor insufflation is intended to take place, the insufflation gas made available by the insufflator escapes to the environment through the opening. Particularly if $CO_2$ is used as insufflation gas, this entails considerable costs, since the storage container, for example a bottle of $CO_2$, is unnecessarily emptied and has to be replaced early on.

EP 1 707 107 A1 discloses an insufflation and irrigation valve which has a cylinder element with an approximately cylindrical bore in which a cylindrical outer plunger is arranged to be movable. A distal portion of an air line is connected to the bottom of the bore, and a proximal portion of the air line and a proximal and a distal portion of a water line are attached at predetermined positions to the side of the cylinder element. An inner plunger is arranged movably in a bore of the outer plunger and, in its interior, has an air channel formed by transverse bores and a longitudinal bore. A base plate is arranged on the underside of the outer plunger, on which base plate a spring is supported that pretensions the inner plunger. The air channel communicates with a hole in the base plate and, when the inner plunger is pressed manually into the outer plunger counter to the force of the spring, communicates with an aperture and a peripheral groove of the outer plunger. In a first position of the outer plunger, the peripheral groove of the outer plunger communicates with the distal portion of the air line, such that, by actuation of the inner plunger, a connection can be produced between the proximal portion and the distal portion of the air line. In a second position of the outer plunger, a connection is produced, via a peripheral groove of the outer plunger, between the proximal portion and the distal portion of the water line.

Since the valve may become soiled during the operation of the insufflation and irrigation valve and, in particular, contamination with bodily fluid cannot be completely ruled out, cleaning and sterilization are necessary in the case of a reusable valve. However, in the described insufflation and irrigation valve, this is possible only to a limited extent. Dismantling is difficult in particular, and it is barely possible to clean the channels formed in the inner plunger. Moreover, the base plate on which the spring bears prevents the central bore of the outer plunger from being cleaned with a brush guided through said bore.

SUMMARY OF THE INVENTION

The object of the present invention is to specify an insufflation and irrigation valve that does not have the abovementioned disadvantages and in particular is of simpler design and/or easier to clean, and also an endoscope having a corresponding insufflation and irrigation valve.

This object is achieved by an insufflation and irrigation valve according to the invention and by an endoscope according to the invention.

An insufflation and irrigation valve according to the invention serves to control the insufflation and the irrigation during a procedure performed with an endoscope and is intended in particular to be arranged in the distal end area of an endoscope, on a handle of the endoscope. However, the insufflation and irrigation valve can also be designed for use on a control unit separate from the endoscope. With the insufflation and irrigation valve, the functions of insufflation and of irrigation can be controlled manually. A valve of this kind is also referred to as a "combined valve" or "dual valve".

The insufflation and irrigation valve comprises a valve housing with a substantially cylindrical bore which is closed off at one end by a bottom. The valve housing can be a separate component which, for example, can be inserted into a housing of the handle of the endoscope. However, the valve housing can also be formed by the housing of the handle itself or by another component of the endoscope or of a control unit or can be designed in one piece with this component.

A gas inlet, a gas outlet, an irrigation medium inlet and an irrigation medium outlet open into the bore of the valve housing. Said inlets and outlets can be connected to connector nozzles, to which lines, for example hoses, for the insufflation gas and the irrigation medium can be attached. However, the gas inlet, the gas outlet, the irrigation medium inlet and/or the irrigation medium outlet can also be connected to feed paths which are formed by cavities provided in the valve housing or in a component enclosing the latter, for example a housing of the handle of the endoscope. The irrigation medium is generally an irrigation liquid, for example physiological saline solution, but can also be a gaseous irrigation medium.

The insufflation and irrigation valve further comprises an outer plunger which is movable in the substantially cylindrical bore of the valve housing between an open position and a closed position as regards the passage of the irrigation medium. In the open position, the irrigation medium inlet has a fluidic connection to the irrigation medium outlet, and, in the closed position, this connection is interrupted. In this context, "fluidic connection" is understood as a connection that permits the flow of a fluid, i.e. a gas or a liquid, in particular, in the case of the fluidic connection of the irrigation medium inlet and the irrigation medium outlet, the flow of a pressurized irrigation liquid from a proximal portion of an irrigation line, attached to the irrigation medium inlet, to a distal portion of the irrigation line, attached to the irrigation medium outlet. The outer plunger is movable manually. In particular, the outer plunger can be pretensioned in the closed position by a spring force and is movable to the open position, counter to the spring force, when pressure is applied by a finger to a valve button of the outer plunger.

Moreover, the insufflation and irrigation valve comprises an inner plunger which is movable relative to the outer plunger in a longitudinal bore of said outer plunger. The longitudinal bore of the outer plunger is open at both ends and is preferably arranged centrally in the outer plunger. In terms of their respective longitudinal axes, the inner plunger and the outer plunger are thus preferably arranged coaxially to each other. The inner plunger is movable relative to the outer plunger between a position near the bottom of the cylindrical bore of the valve housing and a position remote from the bottom. When the inner plunger is in the position remote from the bottom, there is no fluidic connection of the gas inlet to the gas outlet. When the inner plunger is in the position near the bottom and the outer plunger is in the closed position in which the fluidic connection of the irrigation medium is interrupted, there is a fluidic connection of the gas inlet to the gas outlet, i.e. an insufflation gas, made available at a pressure in a proximal portion of an insufflation line attached to the gas inlet, is able to flow into a distal portion of the insufflation line attached to the gas outlet. When the inner plunger is located in the position near the bottom and the outer plunger is in the open position, the fluidic connection of the gas inlet to the gas outlet can be interrupted. By moving the inner plunger relative to the outer plunger, it is thus possible to control the fluidic connection of the gas outlet to the gas inlet in such a way that, in the position remote from the bottom, there is no fluidic connection and, in the position near the bottom, a fluidic connection exists in at least one position of the outer plunger, and insufflation can thus take place.

According to the invention, with respect to the bottom of the cylindrical bore of the valve housing in which the outer plunger is movable, the gas inlet opens into the bore at a location nearer the bottom than the gas outlet. In particular, the gas inlet opens into a bottom area of the bore, for example into the bottom, or into an area adjoining the bottom, of the substantially cylindrical side wall of the bore. The gas outlet opens into the side wall of the bore. If the gas inlet also opens into the side wall, the gas outlet thus opens in at a position which is farther away from the bottom of the bore than is the position of the mouth of the gas inlet.

By virtue of the fact that the gas inlet opens into the bore of the valve housing at a location nearer the bottom than the gas outlet, it is possible, according to the invention, that the pressure of the insufflation gas generated by the insufflator, for example by an insufflation pump, acts in the bottom area of the cylindrical bore of the valve housing in such a way that the inner plunger is in this way prestressed to the position remote from the bottom. In the position of the inner plunger remote from the bottom, the gas outlet is separated from the gas inlet. Thus, according to the invention, the normal position of the insufflation and irrigation valve, namely the position in which no insufflation takes place, can be reached or at least maintained by the pressure generated by the insufflator, without the need for pretensioning of the inner plunger by a spring. In particular, the inner plunger can be moved to and maintained in the position remote from the bottom, which is the closed position in terms of insufflation, solely by the gas pressure generated by the insufflator. A spring for pretensioning the inner plunger to its position remote from the bottom is therefore not necessary. Design and production are simplified in this way, and the insufflation and irrigation valve is easier to clean. Moreover, installation space is not needed for the spring of the inner plunger, as a result of which the overall length of the insufflation and irrigation valve can be reduced.

According to a preferred embodiment of the invention, the connection of the gas inlet to the gas outlet for performing the insufflation is established via a connection channel of the outer plunger, a recess formed on an outer face of the inner plunger and the bottom-side opening of the longitudinal bore. To permit a fluidic connection that is substantially free from leakage, the connection channel of the outer plunger can be limited in the axial direction on both sides by a respective seal, which seals off the outer plunger against the wall of the cylindrical bore of the valve housing. By virtue of the fact that the connection between the gas inlet and the gas outlet can be produced via the connection channel of the outer plunger, the recess formed on the outer face of the inner plunger and the opening of the longitudinal bore of the outer plunger to the bottom-side space of the cylindrical bore of the valve housing, it is possible to create a fluidic connection that has a large cross section and that permits an unobstructed flow of gas and easy cleaning.

Preferably, the recess formed on the outer face of the inner plunger is designed as a peripheral groove or as a tapering which reaches from a bottom-side end portion of the inner plunger to a portion of the inner plunger lying opposite the connection channel of the outer plunger. By virtue of the fact that the recess is designed as a peripheral groove or as tapering, a flow of gas can be ensured independently of a position of rotation of the inner plunger with respect to its longitudinal axis. In this way, it is possible for the inner plunger to be designed without an anti-rotation means, as a result of which the construction of the insufflation and irrigation valve and the production of the inner plunger are further simplified. In particular, it is possible for the inner plunger to be designed as a simple rotation part. Moreover, the cleaning of the inner plunger is made simple, since all the surfaces to be cleaned are directly accessible from outside.

It is also preferable that the insufflation and irrigation valve is designed in such a way that the bottom-side opening of the longitudinal bore of the outer plunger is closed when the inner plunger is in the position remote from the bottom. This makes it easy to interrupt the flow of gas from the gas inlet to the gas outlet when the inner plunger is in the position remote from the bottom. Since the inner plunger is pressed into the position remote from the bottom by the gas pressure provided from the insufflator, it is in this way particularly easy to ensure that the inner plunger, when not actuated by a user, assumes the position remote from the bottom, in which position the insufflation is interrupted.

It is particularly preferable that the bottom-side end of the inner plunger is designed with a valve disk for closing the bottom-side opening of the longitudinal bore. In particular, the inner plunger can cooperate with the bottom-side opening of the longitudinal bore of the outer plunger in the manner of a disk valve, wherein the bottom-side opening of the longitudinal bore is designed as a valve seat. Thus, for example, the bottom-side end of the inner plunger can be designed flat on the underside and conical on the top, wherein the conical top cooperates with a corresponding conical depression in the lower end of the outer plunger in order to seal off the longitudinal bore of the outer plunger. In this way, it is easy to achieve a particularly safe and gas-tight interruption of the fluidic connection of the gas inlet to the gas outlet, which interruption is obtained by the gas pressure provided from the insufflator.

To perform the insufflation, the inner plunger can be pressed manually, counter to the gas pressure, into the longitudinal bore of the outer plunger, such that it is pressed, relative to the outer plunger, from its position remote from the bottom and in particular adopts its position near the bottom. For this purpose, the inner plunger preferably has such a length that, in the position of the inner plunger remote from the bottom, an end remote from the bottom protrudes above an actuation surface of a valve button on which a user exerts pressure with a finger in order to move the outer plunger and, in the position of the inner plunger near the bottom, it terminates substantially flush with the actuation surface of the valve button. Thus, by feeling the protruding end of the inner plunger or a flat surface, a user can easily ascertain whether the inner plunger is located out of its position near the bottom or whether the position of the inner plunger near the bottom is reached. Control of the insufflation and irrigation valve is simplified in this way.

According to a preferred embodiment of the invention, the gas outlet is closed in the open position of the outer plunger. For this purpose, the outer surface of the outer plunger can be designed to close the gas outlet and, for example, can have a corresponding blocking body, if appropriate with seals enclosing the latter. In particular, the open position of the outer plunger is a position in which the outer plunger is near the bottom of the cylindrical bore of the valve housing. Whereas, in accordance with this embodiment of the invention, the gas outlet is thus closed in the open position of the outer plunger, the gas outlet, in the closed position of the outer plunger, can be alternately connected to or separated from the gas inlet by actuation of the inner plunger. In the normal position, in which a user actuates neither the outer plunger nor the inner plunger, it is thereby possible for both the irrigation and also the insufflation to be interrupted. In a second position of the valve, the inner plunger can be pressed into the longitudinal bore of the outer plunger in such a way that the connection between the gas inlet and the gas outlet is opened and, as a result, the gas provided from the insufflator can be conveyed to the distal end of the endoscope. In a third position, the outer plunger is pressed together with the inner plunger into the cylindrical bore of the valve housing, as a result of which, according to this embodiment, the irrigation is activated and the insufflation is interrupted. In intermediate positions, particularly in intermediate positions of the outer plunger between the open position and the closed position, with the inner plunger pressed in to its position near the bottom, it may be possible for both insufflation and also irrigation to be performed simultaneously. This permits particularly simple control of both functions of the insufflation and irrigation valve.

The fluidic connection between the irrigation medium inlet and the irrigation medium outlet is preferably produced via a peripheral groove formed on the outer face of the outer plunger. The axial length of the peripheral groove is chosen in such a way, and the groove arranged in such a way, that the groove corresponds both with the irrigation medium inlet and also with the irrigation medium outlet only in the open position and thereby produces the connection. This permits a connection for performing the irrigation with a particularly large cross section, which connection may also be dependent on a rotation position of the outer plunger relative to the valve housing.

It is moreover preferable that, in the area of the mouth of the irrigation medium inlet, the irrigation medium outlet and/or the gas outlet, the substantially cylindrical bore of the valve housing is widened by a peripheral shallow groove with at least one beveled wall. Otherwise, the bore of the valve housing can be of cylindrical configuration. In this way, the seals provided for sealing off the outer plunger from the cylindrical bore are able to slide with low wear in the bore.

It is also preferable that the gas outlet and, if appropriate, also the irrigation medium outlet are each formed by a opening into the valve housing obliquely with respect to a longitudinal axis of the bore and in particular directed obliquely with respect to the longitudinal axis of the bore. These can be designed as nozzles for the attachment of lines or hoses. In this way, an insufflation and irrigation valve having a particularly space-saving design is made possible.

An endoscope according to the invention has an insufflation and irrigation valve as described above, which in particular is arranged on the handle of the endoscope and can be actuated with a finger by a user of the endoscope. The endoscope can be designed as a rigid, semi-rigid or flexible endoscope. In particular, the endoscope is a gastroscope with an elongate flexible shank and with a handle which is arranged at the proximal end of the shank and which has the insufflation and irrigation valve. The handle can have further control elements, for example a suction valve and control elements for controlling further functions of the endoscope. The gas inlet and the irrigation medium inlet can have connector nozzles for attachment of the proximal portion of an insufflation line and an irrigation line, respectively, through which it is possible to create a connection to a separate insufflator and to a storage container for irrigation medium, which is likewise subject to the pressure provided from the insufflator. The gas outlet and the irrigation medium outlet of the insufflation and irrigation valve are connected to the distal portions of the insufflation line and irrigation line, which extend through the shank of the endoscope to the distal end of the latter. The distal end of the irrigation line can be directed to the distal window of the lens system of the endoscope. A common line for insufflation and irrigation can be provided inside the shank. By virtue of the design of the endoscope according to the invention with the described insufflation and irrigation valve, an endoscope is created in which simple manual control of insufflation and irrigation is possible and in which the insufflation and irrigation valve is of a simple design and is easy to clean.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

Further aspects of the invention will become clear from the following description of a preferred illustrative embodiment and from the attached drawing, in which.

DETAILED DESCRIPTION OF THE INVENTION

Figure 1:
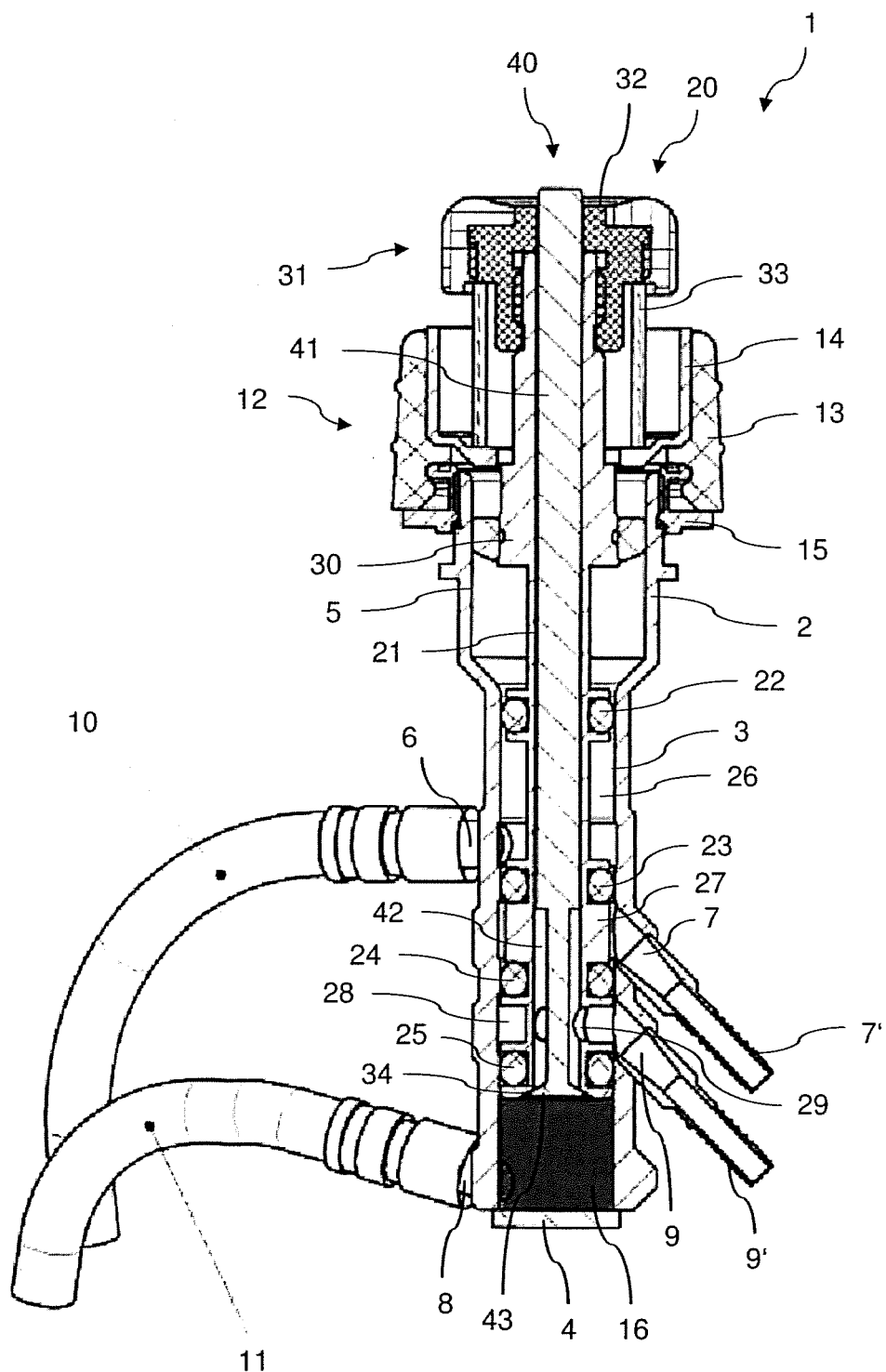
FIG. 1 shows, in longitudinal section, an insufflation and irrigation valve according to an illustrative embodiment of the invention in a first position.

As is shown in FIG. 1, an insufflation and irrigation valve 1 according to an illustrative embodiment of the invention comprises a valve housing 2, which has a substantially cylindrical bore 3. The bore 3 is closed by a bottom 4 at its lower end, and it merges at its upper end into a widened part 5. The bottom 4 can be formed in one piece with the valve housing 2 or it can also be attached to the valve housing 2, for example screwed on or welded on. The valve housing 2 can be inserted into a housing (not shown) of a handle of an endoscope.

An irrigation medium inlet 6, an irrigation medium outlet 7, a gas inlet 8 and a gas outlet 9 open into the side wall of the bore 3. They each have a connector nozzle onto which a corresponding attachment line can be pushed. In FIG. 1, an irrigation hose 10 and an insufflation hose 11 are shown, which each form the proximal portion of an irrigation line and insufflation line, respectively, and which are pushed onto the respective connector nozzle of the irrigation medium inlet 6 or gas inlet 8. During the operation of the insufflation and irrigation valve 1, the irrigation hose 10 is connected, by the end that is not shown, to a storage container for irrigation medium, for example a bag of irrigation liquid, while the insufflation hose 11 is connected to an insufflator (not shown). The insufflator can be an insufflation pump, for example, which makes available an insufflation gas, for instance $CO_2$, at a pressure suitable for the medical insufflation. The storage container for irrigation medium can likewise be subjected to pressure by the insufflator, in particular to the same pressure at which the insufflation gas is made available through the insufflation hose 11, such that the irrigation medium is delivered at the same pressure via the irrigation hose 10.

The distal portion of the irrigation line and of the insufflation line is not shown in FIG. 1. During the operation of the insufflation and irrigation valve 1, corresponding attachment lines are attached to the connector nozzle 7' of the irrigation medium outlet 7 and to the connector nozzle 9' of the gas outlet 9, for example hoses, or also channels which are formed fixedly in the endoscope and through which the irrigation medium and the insufflation gas are guided through the shank as far as the distal end area of the endoscope. The oblique orientation of the connector nozzles 7', 9' in question permits a space-saving arrangement of the insufflation and irrigation valve 1 and of the associated lines or channels. The irrigation line and the insufflation line can open into a common channel in the distal direction from the insufflation and irrigation valve 1.

An outer plunger 20, which is substantially tubular with a continuous central longitudinal bore 21, is inserted into the bore 3. The outer plunger 20 is guided in the bore by four sealing rings 22, 23, 24, 25 which are designed as O-rings and which are each held in peripheral grooves on the outer face of the outer plunger 20. Between the top sealing ring 22 and the second top sealing ring 23, the outer plunger 20 has, on its outer face, a peripheral groove 26 whose width corresponds approximately to the axial distance between the mouth of the irrigation medium inlet 6 and that of the irrigation medium outlet 7. Between the second top sealing ring 23 and the sealing ring 24 second from bottom, the outer plunger 20 has a diameter that almost corresponds to the internal diameter of the bore 3. In this way, the outer plunger 20 in this area forms a blocking body 27, which is suitable for closing the mouth of the irrigation medium outlet 7. Between the sealing ring 24 second from bottom and the very bottom sealing ring 25, a further groove 28 is formed in the outer face of the outer plunger 20, said further groove 28 having at least one aperture 29 that leads to the longitudinal bore 21 and that is formed, for example, by a short transverse bore.

In its upper area, the outer plunger 20 forms a thickened plunger body 30 onto which a plastic cap 31 is fitted that forms a valve button. On its top, the plastic cap 31 has a shallow indentation 32, which constitutes an actuation surface of the valve button. The central longitudinal bore of the outer plunger extends through the plunger body 30 and the plastic cap 31 as far as the center of the indentation 32. The plunger body 30 is guided movably in the widened part 5 of the valve body 2. A head part 12, which comprises a cup-shaped metal part 14 enclosed by a plastic body 13, is mounted on the upper end of the valve housing 2. The plastic body 13 is secured with a union nut 15 on the upper end of the valve housing 2. The metal part 14 has a central bore through which the plunger body 30 protrudes. Between the metal part 14 and the plastic cap 31, a helical spring 33 is fitted which pretensions the outer plunger 20 in its upper position remote from the bottom 4.

An inner plunger 40 is arranged in the cylindrical longitudinal bore 21. The inner plunger 40 comprises a cylindrical stem 41, which has an external diameter corresponding almost to the internal diameter of the longitudinal bore 21 and which is inserted sealingly into said longitudinal bore and is movable therein. In its lower area, the stem 41 has a peripheral groove 42 with a width corresponding at least approximately to the distance of the aperture 29 of the outer plunger 20 from the lower end of the outer plunger 20. The bottom end of the stem 41, i.e. the end directed toward the bottom 4, is provided with a widened part designed as a valve disk 43, which has a conical shape on top and, in the manner of a disk valve, engages sealingly in a corresponding conical indentation serving as a valve seat 34 in the lower end of the outer plunger 20.

In the position shown in FIG. 1, the upper end of the stem 41 of the inner plunger 40 remote from the bottom protrudes above the actuation surface, which is formed by the indentation 32 in the axial surface of the plastic cap 31. In this position, the valve disk 43 of the inner plunger 40 bears sealingly in the valve seat 34 of the outer plunger 20. Insufflation gas, delivered at pressure from an insufflator through the insufflation hose 11 into the lower area of the interior 16 of the valve housing 2, cannot therefore reach the peripheral groove 42 of the inner plunger 40 and, consequently, cannot reach the gas outlet 9. The valve disk 43 is pressed into the valve seat 34 by the pressure of the gas in the interior 16, such that the inner plunger 40 is held in the position shown in FIG. 1, in which the upper end protrudes above the surface of the plastic cap 31. At the same time, the valve disk 43, with the valve seat 34 as an abutment, serves to limit the movement of the inner plunger and to secure the inner plunger 40 in the position remote from the bottom relative to the outer plunger 20.

In the position shown in FIG. 1, the outer plunger 20 is held in its upper position, i.e. remote from the bottom 4, by the helical spring 33, the upward movement being limited by the plunger body 30 and the metal part 14. In addition, the outer plunger 20 is held in this position by the gas pressure prevailing in the interior 16. In this position, the groove 26 corresponds with the irrigation medium inlet 6, but the second top sealing ring 23 is arranged between the irrigation medium inlet 6 and the irrigation medium outlet 7, such that no connection exists to the irrigation medium outlet 7. At the top, the groove 26 is sealed off by the top sealing ring 22, such that loss of irrigation medium is avoided. In the first position of the insufflation and irrigation valve 1 as shown in FIG. 1, which is the normal position, i.e. the non-actuated position, both the irrigation and also the insufflation are thus interrupted.

Figure 2:
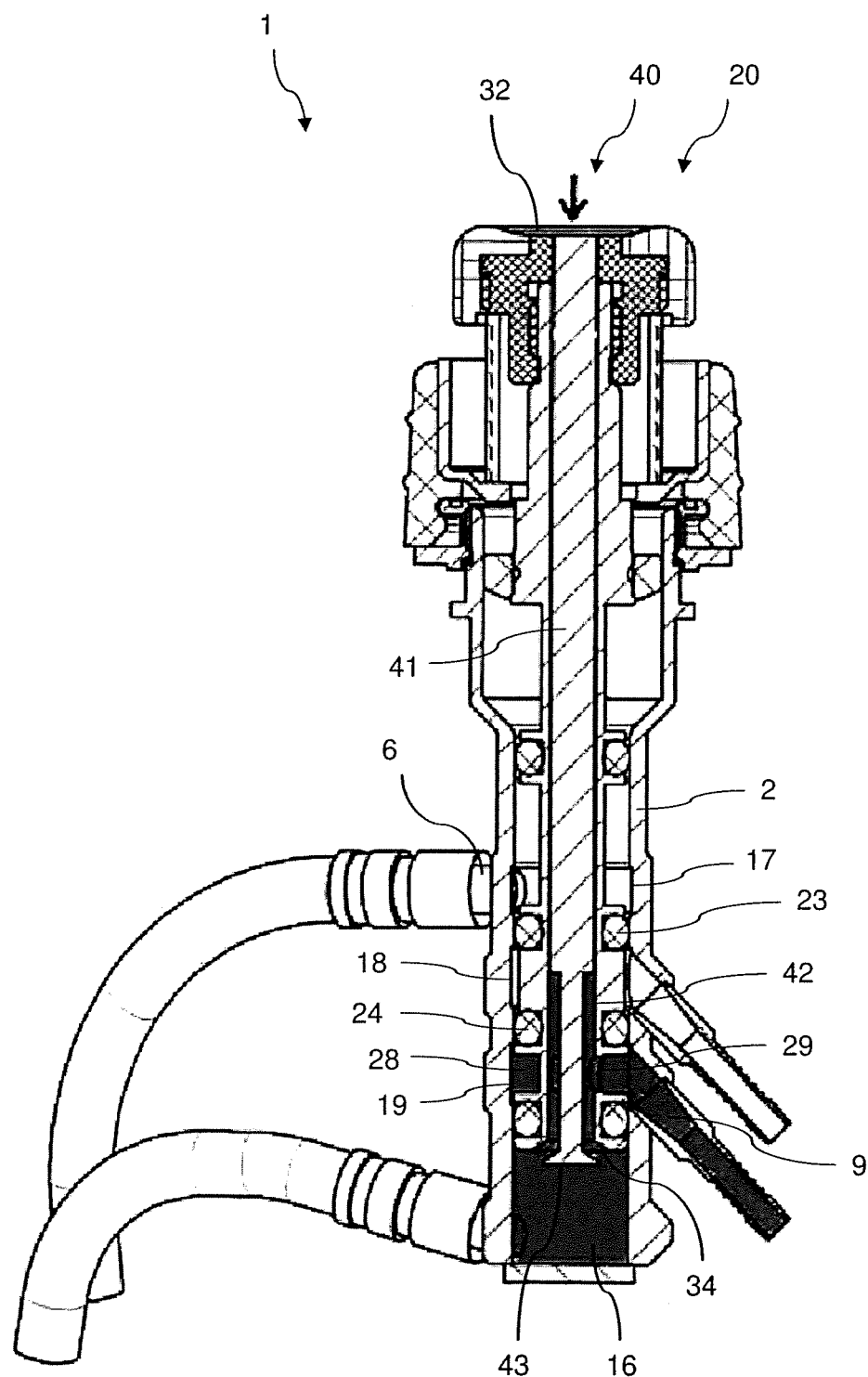
FIG. 2 shows the insufflation and irrigation valve from FIG. 1 in a second position.

To actuate the insufflation and irrigation valve 1, the user places a finger on the actuation surface of the valve button, formed by the shallow indentation 32, and exerts pressure with the finger in order to move the inner plunger 40 and outer plunger 20. In the second position of the insufflation and irrigation valve 1, as shown in FIG. 2, the inner plunger 40 is pressed (as indicated by the arrow), by actuation with the finger, into the outer plunger to such an extent that the upper end of the stem 41 of the inner plunger 40 terminates flush with the surface of the bottom of the indentation 32. In this position, the valve disk 43 is pressed out from the valve seat 34, such that insufflation gas is able to flow (as indicated in FIG. 2) from the interior 16 through the groove 42 of the inner plunger 40 and through a connection channel of the outer plunger 20, formed by the aperture 29 and the groove 28, into the gas outlet 9 and onward to the distal end of the endoscope. In this position, gas insufflation can thus take place. While the inner plunger 40 is thus located in its position near the bottom, the outer plunger is in its position remote from the bottom as in FIG. 1, which is the closure position, and irrigation therefore does not take place.

Figure 3:
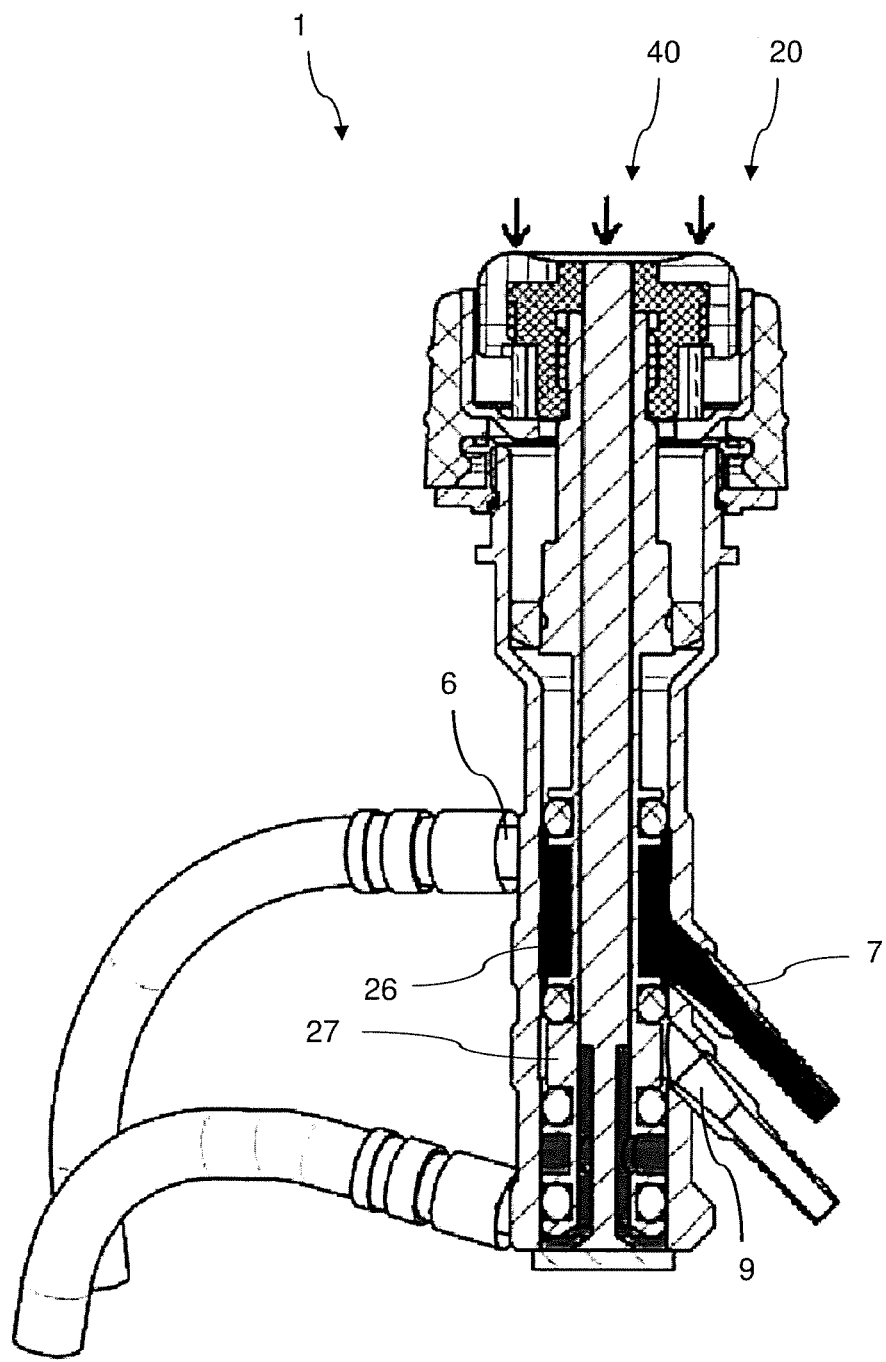
FIG. 3 shows the insufflation and irrigation valve from FIG. 1 in a third position.

In the third position of the insufflation and irrigation valve 1, as shown in FIG. 3, the outer plunger 20 has also been pressed down (as indicated by the three arrows) by the user applying further pressure with the finger. In this position, the groove 26 still corresponds with the irrigation medium inlet 6, but likewise with the irrigation medium outlet 7. Thus, by way of the peripheral groove 26 of the outer plunger 20, a connection is established between the irrigation medium inlet 6 and the irrigation medium outlet 7, and therefore, on account of the pressure with which it is made available in the irrigation medium inlet 6, irrigation medium is able to pass into the irrigation medium outlet 7 and onward to the distal end of the endoscope (as indicated in FIG. 3). Irrigation can therefore take place in this position. As in FIG. 2, the inner plunger 40 is located in its position near the bottom relative to the outer plunger 20, but the gas outlet 9 is now closed by the blocking body 27. Consequently, insufflation does not take place.

In the area of the irrigation medium inlet 6, the irrigation medium outlet 7 and the gas outlet 9, a respective ring-shaped and peripheral shallow groove 17, 18, 19 is formed in the wall of the otherwise cylindrical bore 3 (see FIG. 2). The grooves 17, 18, 19 each have at least partially beveled edges, such that the two middle sealing rings 23, 24, which slide over the edges, are not damaged. In this way, it is possible to avoid damage to the sealing rings 23, 24 as they slide over the edges of the mouths of the irrigation medium inlet 6, the irrigation medium outlet 7 and the gas outlet 9. The wall of the valve body 2 can be strengthened in the corresponding area.

In an intermediate position (not shown in the figures) between the second position (see FIG. 2) and the third position (see FIG. 3) of the insufflation and irrigation valve 1, it is possible for insufflation and irrigation to take place simultaneously, wherein the respective cross sections of flow of the connections between the irrigation medium inlet 6 and the irrigation medium outlet 7 or between the gas inlet 8 and the gas outlet 9 permit sensitive control of both processes. Since the irrigation medium and the insufflation gas are delivered at an almost identical pressure, irrigation medium does not enter the gas outlet 9, and insufflation gas does not enter the irrigation medium outlet 7, to a disruptive extent.

As will be clear from the figures, the head part 12 can be released from the valve housing 2, and the outer plunger 20 removed from the bore 3, by undoing the union nut 15. The inner plunger 40 can then be removed down the way from the longitudinal bore 21. The insufflation and irrigation valve 1 is therefore very easy to dismantle and can be easily cleaned in the dismantled state since all the surfaces to be cleaned are readily accessible. The insufflation and irrigation valve 1 can likewise be easily assembled by a reverse sequence of steps.

For the sake of clarity, not all of the reference signs are shown in all of the figures. Reference signs that are not explained in connection with one figure have the same meaning as in the other figures.

The invention claimed is:

1. An insufflation and irrigation valve for an endoscope, comprising:
   a valve housing with a substantially cylindrical bore;
   a bottom closing off the bore at one end thereof;
   a gas inlet opening into the bore;
   a gas outlet opening into the bore;
   an irrigation medium inlet opening into the bore;
   an irrigation medium outlet opening into the bore;
   an outer plunger which is movable in the bore between an open position, in which the irrigation medium outlet is fluidically connected to the irrigation medium inlet, and a closed position, in which the irrigation medium outlet is separated from the irrigation medium inlet, the outer plunger having a longitudinal bore extending from a top-side opening to a bottom-side opening of the outer plunger; and
   an inner plunger which is movable in the longitudinal bore of the outer plunger in order to permit a fluidic connection of the gas outlet to the gas inlet in a first position and in order to interrupt the fluidic connection of the gas outlet to the gas inlet in a second position, wherein the inner plunger is closer to the bottom in the first position than in the second position;

wherein the gas inlet opens into the bore of the valve housing at a location nearer the bottom than the gas outlet;

wherein the bottom-side opening of the outer plunger is closed when the inner plunger is in the second position; and wherein a bottom-side end of the inner plunger is designed with a valve disk for closing the bottom-side opening of the outer plunger.

2. The insufflation and irrigation valve according to claim 1, wherein the gas outlet and the gas inlet are connectable via a connection channel of the outer plunger, a recess formed on an outer face of the inner plunger and a portion of the longitudinal bore proximate the bottom-side opening of the outer plunger.

3. The insufflation and irrigation valve according to claim 2, wherein the recess formed on the outer face of the inner plunger is designed as a peripheral groove or tapering.

4. The insufflation and irrigation valve according to claim 1, wherein the inner plunger has such a length that, in the second position, an end of the inner plunger remote from the bottom protrudes above an actuation surface of a valve button of the outer plunger and, in the first position, terminates flush with the actuation surface of the valve button.

5. The insufflation and irrigation valve according to claim 1, wherein the gas outlet is closed by the outer plunger in the open position of the outer plunger.

6. The insufflation and irrigation valve according to claim 1, wherein, in an area of a mouth of the irrigation medium inlet, the irrigation medium outlet and/or the gas outlet, the bore of the valve housing is widened by a peripheral groove with at least one beveled wall.

7. The insufflation and irrigation valve according to claim 1, wherein the gas outlet is formed by a channel directed obliquely with respect to the longitudinal axis of the bore.

8. An endoscope, comprising:
an insufflation and irrigation valve including:
a valve housing with a substantially cylindrical bore;
a bottom closing off the bore at one end thereof;
a gas inlet opening into the bore;
a gas outlet opening into the bore;
an irrigation medium inlet opening into the bore;
an irrigation medium outlet opening into the bore;
an outer plunger which is movable in the bore between an open position, in which the irrigation medium outlet is fluidically connected to the irrigation medium inlet, and a closed position, in which the irrigation medium outlet is separated from the irrigation medium inlet, the outer plunger having a longitudinal bore extending from a top-side opening to a bottom-side opening of the outer plunger; and an inner plunger which is movable in the longitudinal bore of the outer plunger in order to permit a fluidic connection of the gas outlet to the gas inlet in a first position and in order to interrupt the fluidic connection of the gas outlet to the gas inlet in a second position, wherein the inner plunger is closer to the bottom in the first position than in the second position;

wherein the gas inlet opens into the bore of the valve housing at a location nearer the bottom than the gas outlet;

wherein the bottom-side opening of the outer plunger is closed when the inner plunger is in the second position; and wherein a bottom-side end of the inner plunger is designed with a valve disk for closing the bottom-side opening of the outer plunger.

9. The insufflation and irrigation valve according to claim 1, wherein the inner plunger is a solid cylindrical stem having an external diameter corresponding to an internal diameter of the longitudinal bore of the outer plunger.

10. The insufflation and irrigation valve according to claim 1, wherein the inner plunger is at least maintained in the second position by a pressure generated by an insufflator.

11. The insufflation and irrigation valve according to claim 1, wherein the gas inlet and the gas outlet are nearer to the bottom than are the irrigation medium inlet and the irrigation medium outlet.

12. The insufflation and irrigation valve according to claim 1, wherein a first distance extends between the gas inlet and the bottom, a second distance extends between the gas outlet and the bottom, a third distance extends between the irrigation medium inlet and the bottom, and a fourth distance extends between the irrigation medium and the bottom; and wherein the first and second distances are less than the third and fourth distances.

* * * * *